US011927587B2

(12) United States Patent
Xiao et al.

(10) Patent No.: US 11,927,587 B2
(45) Date of Patent: Mar. 12, 2024

(54) THROMBELASTOGRAPHY DEVICE, HEATING APPARATUS, BLOOD COAGULATION ANALYSIS SYSTEM AND ROTATIONAL ANGLE MEASUREMENT METHOD

(71) Applicant: Haemonetics Corporation, Boston, MA (US)

(72) Inventors: Jian Xiao, Jiangsu (CN); Aiqin Chen, Jiangsu (CN); Bangzhong Yu, Jiangsu (CN); Feng Jiang, Jiangsu (CN)

(73) Assignee: Haemonetics Corporation, Boston, MA (US)

( * ) Notice: Subject to any disclaimer, the term of this patent is extended or adjusted under 35 U.S.C. 154(b) by 0 days.

(21) Appl. No.: 17/748,679

(22) Filed: May 19, 2022

(65) Prior Publication Data
US 2022/0283142 A1 Sep. 8, 2022

Related U.S. Application Data

(62) Division of application No. 16/096,956, filed as application No. PCT/CN2017/082777 on May 2, 2017, now Pat. No. 11,366,094.

(30) Foreign Application Priority Data

May 24, 2016 (CN) .......................... 201610347496.9
May 24, 2016 (CN) .......................... 201610347497.3
(Continued)

(51) Int. Cl.
*G01N 33/49* (2006.01)
*B01L 3/00* (2006.01)
(Continued)

(52) U.S. Cl.
CPC .......... *G01N 33/4905* (2013.01); *B01L 3/502* (2013.01); *B01L 7/00* (2013.01);
(Continued)

(58) Field of Classification Search
CPC ......... G01N 33/4905; G01N 2011/147; G01N 33/86; G01N 11/14; G01N 33/49;
(Continued)

(56) References Cited

FOREIGN PATENT DOCUMENTS

CN 104181311 B * 2/2016 ............. G01N 33/86

OTHER PUBLICATIONS

CN-104181311-B Google translation (Jul. 2, 2023) (Year: 2014).*

* cited by examiner

*Primary Examiner* — Dean Kwak
(74) *Attorney, Agent, or Firm* — Nutter McClennen & Fish LLP (57) ABSTRACT

A thrombelastography device, a heating apparatus, a blood coagulation analysis system, and a rotational angle measurement method are disclosed. The thrombelastography device consists of a plurality of thrombelastography device splits (2) that are horizontally arranged in parallel. The thrombelastography device split (2) comprises a worktable (4), a rack (5), a test bar (6), a tester (8), and a processor (9). The thrombelastography device overcomes the defect in the prior art that the measurement result of a thrombelastography device is inaccurate. The amount of reflected light is used as a reference for thrombelastographic evaluation, and thus the result is more accurate.

4 Claims, 8 Drawing Sheets

(30) Foreign Application Priority Data

May 24, 2016 (CN) .......................... 201620477344.6
May 24, 2016 (CN) .......................... 201620477597.3

(51) Int. Cl.
*B01L 7/00* (2006.01)
*B01L 9/02* (2006.01)
*G01N 11/00* (2006.01)
*G01N 11/14* (2006.01)

(52) U.S. Cl.
CPC ................ *B01L 9/02* (2013.01); *G01N 11/14* (2013.01); *B01L 2200/025* (2013.01); *B01L 2300/0654* (2013.01); *B01L 2300/168* (2013.01); *B01L 2300/1805* (2013.01); *G01N 11/00* (2013.01)

(58) Field of Classification Search
CPC .... G01N 11/142; G01N 11/162; G01N 11/00; B01L 2200/025; B01L 2300/0654; B01L 2300/168; B01L 2300/1805; B01L 3/502; B01L 7/00; B01L 9/02
See application file for complete search history.

THROMBELASTOGRAPHY DEVICE, HEATING APPARATUS, BLOOD COAGULATION ANALYSIS SYSTEM AND ROTATIONAL ANGLE MEASUREMENT METHOD

CROSS-REFERENCE TO RELATED APPLICATIONS

This is a divisional of U.S. patent application Ser. No. 16/096,956, filed Oct. 26, 2018, which is a is national phase entry under 35 U.S.C. § 371 of Patent Cooperation Treaty Application Serial No. PCT/CN2017/082777, which claims priority to Chinese national application no. 201610278393.1, filed Apr. 29, 2016, Chinese national application no. 201620383166.0, filed Apr. 29, 2016, Chinese national application no. 201620477344.6, filed May 24, 2016, Chinese national application no. 201610347497.3, filed May 24, 2016, Chinese national application no. 201610347496.9, filed May 24, 2016, and Chinese national application no. 201620477597.3, filed May 24, 2016, each of which is incorporated by reference herein in its entirety.

TECHNICAL FIELD

The present invention relates to the technical field of measurement, in particular, to a thrombelastography device, a heating apparatus, a blood coagulation analysis system, and a rotational angle measurement method.

BACKGROUND

A thrombelastography device is an apparatus for measuring blood coagulation in vitro. When human blood is drawn from the human body, it is possible to produce a series of changes in state such as coagulation and fibrinolysis. Through clinical monitoring, there is a significant difference in the state of blood between normal human blood and morbid (cardio-cerebral vascular disease) human blood throughout the process. This significant difference is mainly reflected in the rates of coagulation and fibrinolysis and the strength of coagulation. This difference in rate and strength can provide objective guidance for the clinical diagnosis of diseases such as cardiovascular and cerebrovascular diseases. The detection principle of the thrombelastography device is to detect and analyze the physical characteristics (rate, strength, etc.) of human blood. Different from other blood coagulation detection and analysis device which measures time segments of the blood coagulation process only, the thrombelastography device can reflect the whole blood coagulation of the human body, that is, the entire coagulation and fibrinolysis process.

SUMMARY

An objective of the present invention is to provide a thrombelastography device which has high measurement precision.

In order to solve the above problems, according to an aspect of the present invention, there is provided a thrombelastography device which consists of a plurality of thrombelastography device splits that are horizontally arranged in parallel, wherein each of the thrombelastography device splits comprises:

a worktable which is used for supporting a container for containing blood and comprises a power device driving the container to rotate;

a rack fixed on the worktable;

a test bar which is located above the container, able to be at least partially inserted into the blood in the container and rotatably connected to the rack, wherein the side surface of the test bar is further provided with a reflective surface; and a tester which is fixedly connected to the rack and provided with a first through hole that allows the test bar to passes through and is arranged vertically, and at least two horizontal second through holes which are communicated with the first through hole, wherein the reflective surface is located in the first through hole, a light emitting device and a light receiving device are arranged inside the at least two second through holes respectively, the light emitting device is able to emit light to the reflective surface, and the light receiving device is able to receive light reflected by the reflective surface.

According to another aspect of the present invention, there is provided a position correction device for a thrombelastography device, wherein the thrombelastography device comprises a rack and a test bar; the rack is connected to one end of the test bar; the rack is used for supporting the test bar, such that the other end of the test bar can be placed in measured blood; the test bar is configured to be able to rotate under a driving force of the measured blood;

the position correction device comprises at least one hair spring, wherein an inner ring of each of the hair springs is fixedly connected to the outer circumferential surface of the test bar, and an outer ring of each of the hair spring is fixedly connected to the rack, and the position correction device is used for generating, when the test bar rotates away from a balanced position, an acting force for rotating the test bar back to the balanced position.

According to yet another aspect of the present invention, there is provided a thrombelastography device, comprising a rack, a test bar and the correction device as described above.

According to a further aspect of the present aspect, there is provided a use method for the thrombelastography device, which comprises:

supporting the test bar by the rack, such that one end of the test bar is placed in the measured blood;

driving the test bar by the measured blood, such that the test bar rotates; and generating, by the position correction device when the test bar rotates away from a balanced position, an acting force for restoring the test bar to the balanced position.

According to a yet further aspect of the present invention, there is provided a heating apparatus, comprising a container for containing liquid;

at least one heater which is in contact with the container and used for heating the liquid in the container; and a temperature controller which is connected to the at least one heater, and used for collecting a current temperature of each heater and performing heating control on each heater according to the current temperature of each heater and a pre-stored set temperature.

According to a further aspect of the present invention, there is provided a blood coagulation analysis system, comprising the heating apparatus as described above and a thrombelastography device, wherein the thrombelastography device is used for performing coagulation analysis on blood in the container of the heating apparatus.

The present invention has the following beneficial effects: in the thrombelastography device provided by the embodiment of the present invention, the power device drives the container to rotate; because the blood in the container has a certain viscosity, it will drive the test bar to rotate, and the reflective surface arranged on the test bar will also rotate; the positions of the light receiving device and the light reflecting device are fixed, so the amount of light that is incident on the reflective surface changes, and the amount of light that can be received among the light reflected by the reflective surface changes. The elastic force of the blood is evaluated according to the amount of change in the finally received light, so the accuracy is high with respect to a conventional sensor.

The embodiments of the present invention further provide a heating apparatus and a coagulation analysis system. The liquid in the container is heated by contacting at least one heater to the container. The current temperature of each heater is collected by the temperature controller. The heater is subjected to heating control according to the pre-stored set temperature to ensure that the temperature of the heater is kept to a preset temperature. The heater can ensure, by heat transfer, that the liquid in the container is also kept to the set temperature, thereby achieving automatic heating control and further reducing the cost.

BRIEF DESCRIPTION OF THE DRAWINGS

In order to more clearly illustrate the embodiments of the present invention or the technical solutions in the prior art, the drawings used in the embodiments or the prior art description will be briefly described below. Apparently, the drawings in the following description are some embodiments of the present invention. For those of ordinary skill in the art, other drawings may also be obtained according to these drawings, without paying creative work.

In drawings, numerical symbols represent the following components: 2—thrombelastography device split; 3—container; 4—worktable; 5—rack; 6—test bar; 7—reflective surface; 8—tester; 10—first through hole; 12—second through hole; 14—light emitting device; 16—light receiving device; 18—first support; 20—second support; 22—upright column; 24—first crossbeam; 26—second crossbeam; 28—top cone; 30—jewel bearing; 32—light guide column; 34—light blocking sheet; 36—hair spring.

DETAILED DESCRIPTION

In order to make the objective, the technical solution and the advantages of the embodiments of the present invention clearer, the technical solutions in the embodiments of the present invention are clearly and completely described below with reference to the accompanying drawings in the embodiments of the present invention. It is apparent that the described embodiments are part of the embodiments of the present invention, rather than all of the embodiments. All other embodiments obtained by those of ordinary skill in the art based on the embodiments of the present invention without paying creative work should fall within the protection scope of the present invention.

Figure 13:
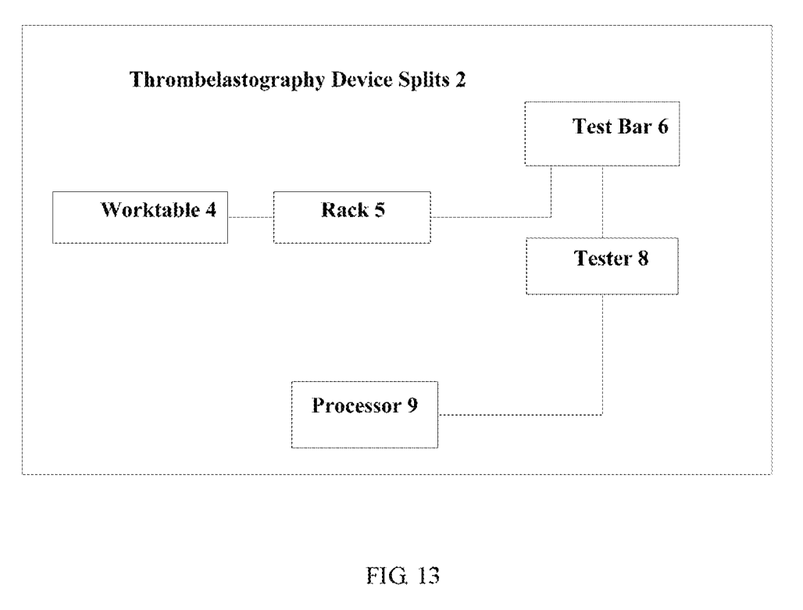
FIG. 13 illustrates a schematic block diagram of thrombelastography device splits in FIG. 1 according to an embodiment of the present invention.

The thrombelastography device of the present invention consists of a plurality of thrombelastography device splits 2 that are horizontally arranged in parallel. FIG. 13 illustrates a compositional block diagram of the thrombelastography device splits. As shown in FIG. 13, each of the thrombelastography device splits comprises: a worktable 4 which is used for supporting a container for containing blood, a rack 5 fixed on the worktable 4, a test bar 6 which is located above the container, a tester 8 which is fixedly connected to the rack 5 and a processor 9 for generating blood coagulation parameter information.

Figure 1:
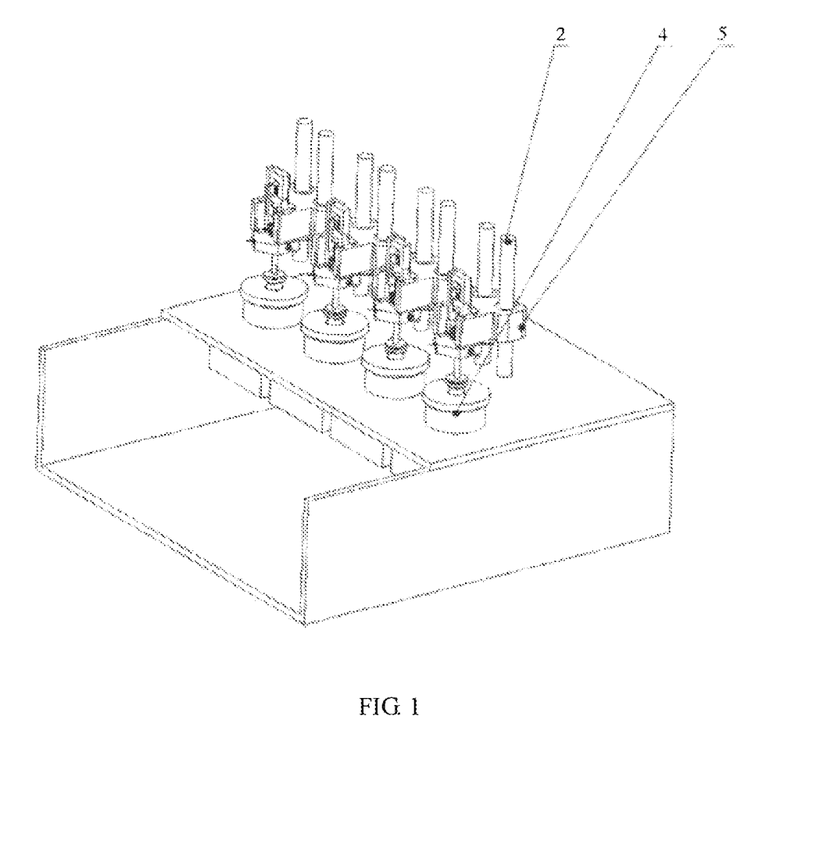
FIG. 1 is a structural schematic diagram of the present invention.
Figure 2:
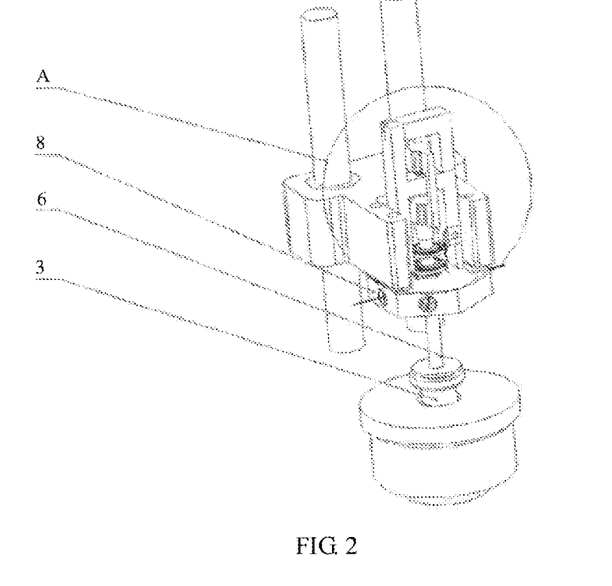
FIG. 2 is a structural schematic diagram of thrombelastography device splits in FIG. 1.

As shown in FIG. 1, each thrombelastography device split 2 comprises:
  a worktable 4 which is used for supporting a container 3 that is arranged thereon and used for containing blood and comprises a power device for driving the container 3 to rotate, wherein a heating apparatus and a controller that can control the heater to heat blood in the container 3 to a set temperature are arranged in the container 3;
  a rack 5 fixed on the worktable 4;
  a test bar 6 which is located right above the container 3, able to be at least partially inserted into the blood in the container 3 and rotatably connected to the rack 5, wherein the side surface of the test bar 6 is further provided with a vertical reflective surface 7; and
  a tester 8 which is fixedly connected to the rack 5 and provided with a first through hole 10 that allows the test bar 6 to passes through and is arranged vertically, and at least two second through holes 12 which are arranged horizontally and communicated with the first through hole 10, wherein the reflective surface 7 is located in the first through hole 10, a light emitting device 14 and a light receiving device 16 are arranged inside the at least two second through holes respectively, the light emitting device 14 is able to emit straight light to the reflective surface 7, and the light receiving device 16 is able to receive straight light reflected by the reflective surface 7; and
  a processor which is able to convert the amount of straight light received by the light receiving device 16 into parameter information reflecting blood coagulation, the parameter information being directly proportional to the amount of light received by the light receiving device 16.

The power device drives the container 3 to rotate. Because the blood in the container 3 has a certain viscosity, it will drive the test bar 6 to rotate, and the reflective surface 7 on the test bar 6 will also rotate. The positions of the light receiving device 16 and the light reflecting device are fixed, so the amount of light that is incident on the reflective surface 7 changes, and the amount of light that can be received among the light reflected by the reflective surface 7 changes. The elastic force of the blood is evaluated according to the amount of change in the finally received light, so the accuracy is high with respect to a conventional sensor. As a further improvement of the present invention, the rack 5 comprises a first support 18 fixedly connected to the tester 8 and a second support 20 fixedly connected to the test bar 6, wherein the first support 18 comprises two upright columns 22 which are fixed on the tester 8 and arranged vertically, and a first crossbeam 24 which is used for connecting the two upright columns 22 and arranged horizontally; the second support 20 comprises an opening through which the first crossbeam 24 passes, and a second crossbeam 26 which is located right above the first crossbeam 24 and is arranged horizontally; a top cone 28 which protrudes downward is arranged in the middle of the lower surface of the second crossbeam 26; a jewel bearing 30 is arranged on the upper surface of the first crossbeam 24; the jewel bearing 30 is located right below the top cone 28; the top cone 28 is in point contact with a concave hole in the jewel bearing 30.

The top cone 28 is arranged on the lower surface of the second crossbeam 26. The jewel bearing 30 is arranged on the upper surface of the first crossbeam 24 which is arranged fixedly. The top cone 28 is located in the concave hole of the jewel bearing 30, and is in point contact with the concave hole. Therefore, the frictional force between the jewel bearing 30 and the top cone 28 is greatly reduced, which means that the resistance to the rotation of the test bar 6 is greatly reduced.

As a further improvement of the present invention, magnets are oppositely arranged on the upper surface of the first crossbeam 24 and the lower surface of the second crossbeam 26, and the opposite surfaces of the magnets have like magnetic poles.

The magnets which have the same magnetism are arranged on the upper surface of the first crossbeam 24 and the lower surface of the second crossbeam 26. It is well known that like magnetic poles of magnets are mutually repulsive, however, the first crossbeam 24 is arranged fixedly, and the magnet on the first crossbeam 24 provides an upward repulsive force to the magnet on the second crossbeam 26. This force acts on the second crossbeam 26 to offset a portion of the gravity of the second crossbeam 26 and the test bar 6, thereby reducing the point friction force between the jewel bearing 30 and the top cone 28, and further reducing the resistance to the rotation of the test bar 6.

As a further improvement of the present invention, two reflective surfaces 7 are arranged to be parallel to each other; four second through holes 12 are arranged to respectively accommodate two light emitting devices or two light receiving devices respectively.

Two sets of light loops are formed to ensure the amount of light received by the light receiving device 16. As a further improvement of the present invention, a hollow light guide column 32 is arranged in the second through holes 12 respectively; the light emitting device 14 or the light receiving device 16 is located in the light guide column 32; the light emitting device 14 is a light emitting diode.

The light guide column 32 is provided to increase the light intensity in the center and have an effect of concentrating light.

As a further improvement of the present invention, a photoelectric source is connected to the light receiving device 16; an amplified circuit board and an AD converter are electrically connected to the photoelectric source in sequence; the AD converter is connected to the processor.

The photoelectric source which serves as the light receiving device 16 is simple and highly-efficient.

As a further improvement of the present invention, a light blocking sheet 34 which is able to block the light guide column 32 from the reflective surface 7 is arranged at one end, close to the first through hole 10, of the light guide column 32; the light blocking sheet 34 is provided with a light outgoing hole; the light blocking sheet 34 is able to limit the light to pass through the light outgoing hole only.

The light blocking sheet 34 and the light outgoing hole are provided for concentrating light.

As a further improvement of the present invention, the thrombelastography device further comprises a position correction device. The thrombelastography device comprises a rack and a test bar; the rack is connected to one end of the test bar; the rack is used for supporting the test bar, such that the other end of the test bar can be placed in measured blood; the test bar is configured to be able to rotate under a driving force of the measured blood; the position correction device is connected to the test bar and used for generating, when the test bar rotates away from a balanced position, an acting force for rotating the test bar back to the balanced position.

Figure 3:
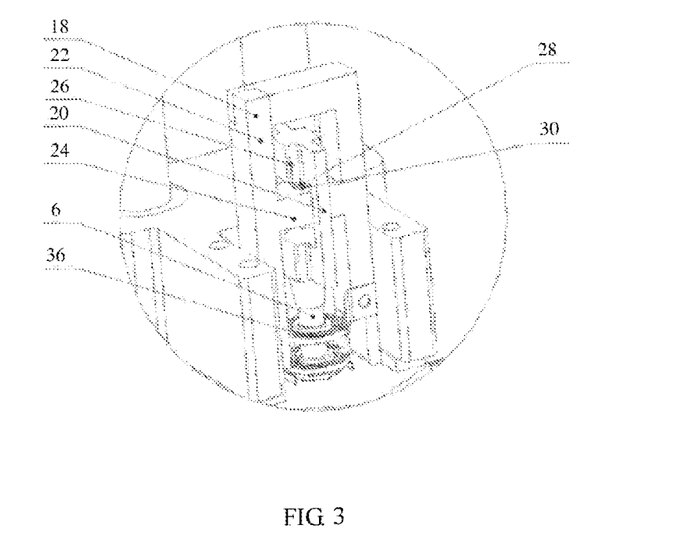
FIG. 3 is a partial sectional view of FIG. 2.
Figure 4:
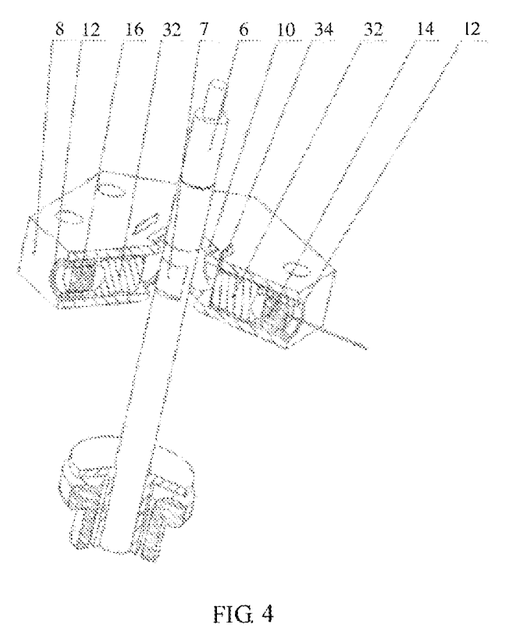
FIG. 4 is a locally enlarged view of A in FIG. 2.

In an embodiment, as shown in FIG. 3, the position correction device may at least one hair spring 36, wherein an inner ring of each of the hair springs 36 is fixedly connected to an outer circumferential surface of the test bar 6, and an outer ring of each of the hair springs 36 is fixedly connected to the upright column 22 of the first support. In the embodiment shown in FIG. 3, the hair spring 36 is provided to play a role of deceleration and buffering, thereby ensuring the stability of numerical values. In addition, after the blood stops rotating, the force acting on the test bar 6 disappears. The hair spring 36 releases a deformation force to return to the original state, and the test bar 6 returns to the fixed initial position.

When the test bar 6 is in the balanced position, the hair spring 36 is in a free state, and does not exert an acting force on the test bar 6. When the test bar 6 rotates under the driving force of the measured blood, the hair spring 36 rotates inward to deform or outward to deform. The hair spring 36 restores an elastic force after being deformed, and the function of restoring the elastic force is to restore the test bar 6 to the balanced position, such that the hair spring 36 restores to the free state. When the driving force of the measured blood on the test bar 6 is removed, if the position where the test bar 6 is located is not the balanced position, the test bar 6 rotates towards the balanced position as the hair spring 36 restores the elastic force, and finally the test bar 6 restores to the balanced position.

In an embodiment of the present invention, when the position correction device comprises at least two hair springs, the spiral direction of at least one hair spring among all the hair springs from the inner ring to the outer ring is opposite to the spiral direction of the other hair spring from the inner ring to the outer ring.

Figure 5:
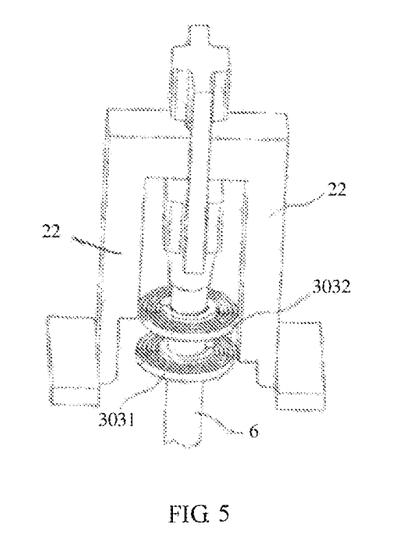
FIGS. 5 and 6 are structural schematic diagrams of different embodiments of a position correction device.

As shown in FIG. 5, the position correction device comprises a hair spring 3031 and a hair spring 3032, wherein inner rings of the hair spring 3031 and the hair spring 3032 are fixed to the test bar 6 respectively, and outer rings of the hair spring 3031 and the hair spring 3032 are fixed to the upright column 22 respectively. As viewed from an observation position shown in FIG. 5, the spiral direction of the hair spring 3031 from the inner ring to the outer ring is clockwise, and the spiral direction of the hair spring 3032 from the inner ring to the outer ring is counterclockwise. When the test bar 6 rotates counterclockwise, the hair spring 3031 is screwed, and when the test bar 302 rotates clockwise, the hair spring 3032 is screwed.

Since the hair spring outputs a stable acting force when it is screwed than the acting force output when it is unscrewed, the hair spring is set to a different spiral direction. When the rotary shaft rotates in different directions, there is always a corresponding hair spring that is screwed to provide an acting force for the rotary shaft to return to the balanced position. By means of such a structure, on the one hand, the test bar rotates more stably, and on the other hand, the plastic deformation caused by excessive unscrewing of the hair spring can be avoided.

In an embodiment of the present invention, the position correction device further comprises at least one zero setting module, wherein each zero setting module corresponds to one hair spring. One end of each zero setting module is fixedly connected to the support, and the other end of the zero setting module is fixedly connected to different positions on the outer ring of the corresponding hair spring in an adjustable manner.

Figure 6:
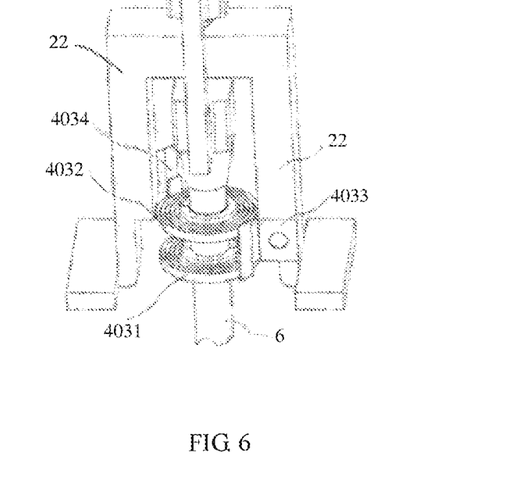

As shown in FIG. 6, the position correction device comprises a hair spring 4031, a hair spring 4032, a zero selling device 4033, and a zero setting device 4034, wherein the hair spring 4031 corresponds to the zero setting device 4033, and the hair spring 4032 corresponds to the zero setting device 4034. One end of the zero setting device 4033 is fixedly connected to the upright column 22, and the other end of the zero setting device 4033 is fixed to the outer ring of the hair spring 4031 by a U-shaped structure. A position, which is fixed to the U-shaped structure, on the outer ring of the hair spring 4031, is adjustable. One end of the zero setting device 4034 is fixedly connected to the upright column 22, and the other end of the zero setting device is fixed to the outer ring of the hair spring 4032 by a U-shaped structure. A position, which is fixed to the U-shaped structure, on the outer ring of the hair spring 4032, is adjustable. The inner rings of the hair spring 4031 and the hair spring 4032 are fixe to the outer circumferential surface of the test bar 6.

By adjusting the position, which is fixed to the outer ring of the hair spring 4031, on the U-shaped structure on the zero setting device 4033, as well as the position, which is fixed to the outer ring of the hair spring 4032, on the U-shaped structure on the zero setting device 4034, the acting force applied by the two hair springs on the test bar 6 when the test bar 6 is not subjected to an external driving force is changed, and the balanced position of the test bar 6 is adjusted, such that the balanced position of the test bar 6 is corrected when the balanced position of the test bar 6 deviates from a target position.

According to an embodiment of the present invention, there is provided a use method for the thrombelastography device as describe above, comprising:
supporting the test bar by the rack, such that one end of the test bar is placed in the measured blood:
driving the test bar by the measured blood, such that the test bar rotates; and
generating, by the position correction device when the test bar rotates away from a balanced position, an acting force for restoring the test bar to the balanced position.

Figure 7:
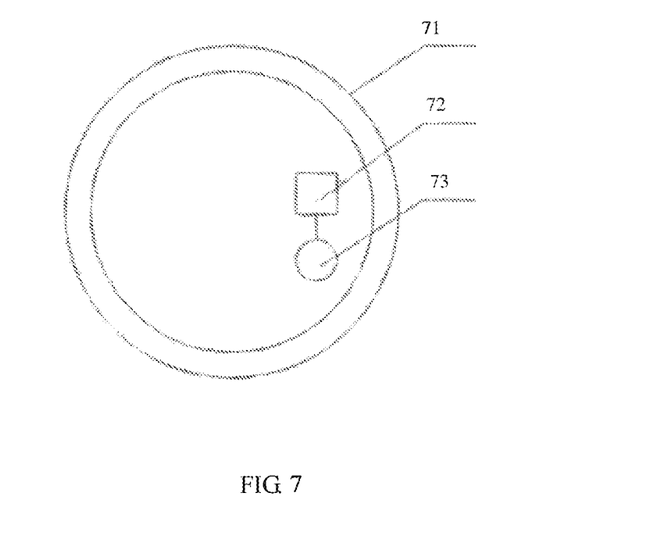
FIG. 7 is a structural schematic diagram of a heating apparatus provided by an embodiment of the present invention.

As shown in FIG. 7, an embodiment of the present invention provides a heating apparatus. The heating apparatus may comprise the following contents:
a container 71 for containing liquid;
at least one heater 72 which is in contact with the container 71 and used for heating the liquid in the container 71; and
a temperature controller 73 which is connected to the at least one heater 72, and used for collecting a current temperature of each heater 72 and performing heating control on each heater 72 according to the current temperature of each heater 72 and a pre-stored set temperature.

According to the heating apparatus, the liquid in the container 71 is heated by arranging at least one heater 72 on the container 71. The current temperature of each heater 72 is collected by the temperature controller 73. The heater 72 is subjected to heating control according to the pre-stored set temperature to ensure that the temperature of the heater 72 is kept to a set temperature. The heater 72 can ensure, by heat transfer, that the liquid in the container 71 is also kept to the set temperature, thereby achieving automatic heating control and further reducing the cost.

At least one heater 72 is electrically connected to the temperature controller 73. The liquid in the container 71 may be blood, medical liquor, water or other liquid.

Figure 8:
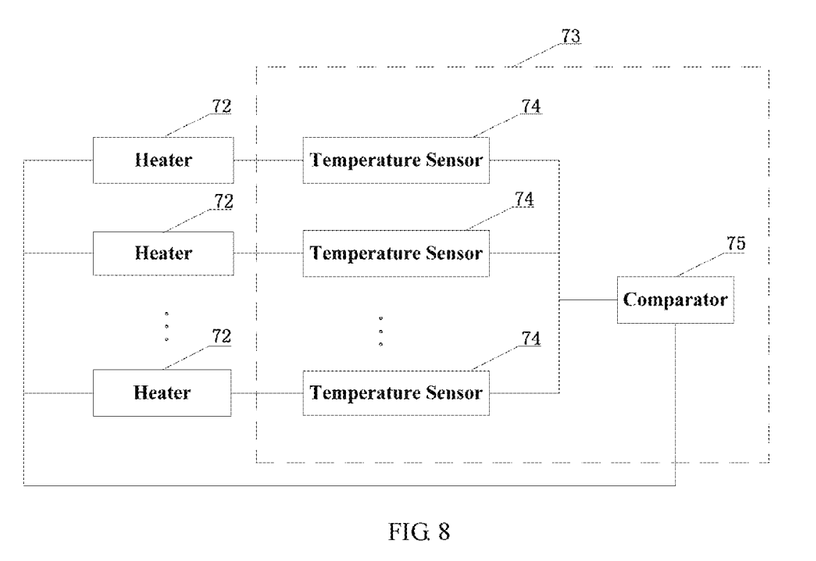
FIG. 8 is a structural schematic diagram of another heating apparatus provided by an embodiment of the present invention.

In an embodiment of the present invention, referring to FIG. 8, the temperature controller 73 may comprise at least one temperature sensor 74 which is connected to the at least one heater 72 in a one-to-one correspondence manner, and used for collecting a current temperature of the heater 72 connected thereto, and outputting the collected current temperature of each heater 72 to a comparator 75; and
the comparator 75 which is connected to the at least one temperature sensor 74 and at least one heater 72, and used for performing heating control on each heater 72 according to the current temperature of each heater 72 and the pre-stored set temperature.

Specifically, the comparator 75 is configured to compare the current temperature value of each heater 72 with a pre-stored set temperature, control a target heater to continue to heat when the current temperature value of the target heater is less than the set temperature and control the target heater to stop heating when the current temperature value of the target heater is not less than the set temperature.

Since the temperature value of the target heater is relatively small during a period of time after the comparator 75 controls the target heater to continue to heat or stop heating, it is not possible to collect the temperature value of the target heater during this period of time. Therefore, in an embodiment of the present invention, the comparator 75 can delay the start of a period of time after controlling the target healer to continue to heal or slop heating. For example, the delay time may be 1 minute. After the delay time has elapsed, the current temperature of the target heater continues to be collected.

In an embodiment of the present invention, the temperature sensor 74 may be a sensor that directly outputs a temperature value, may be a sensor that outputs a voltage value, or may be a sensor that outputs a resistance value.

When the temperature sensor 74 is the sensor that directly outputs the temperature value, the collected temperature value of the heater may be directly output to the comparator 75.

When the value output by the temperature sensor 74 is not a temperature value, it is necessary to convert the output value into a temperature value which is then output to the comparator 75.

The heating apparatus of the present invention will be described with the temperature sensor 74 comprising a thermistor 74 as an example.

In an embodiment of the present invention, the thermistor 74 is used for outputting a current resistance value based on the current temperature of the heater connected thereto.

Figure 9:
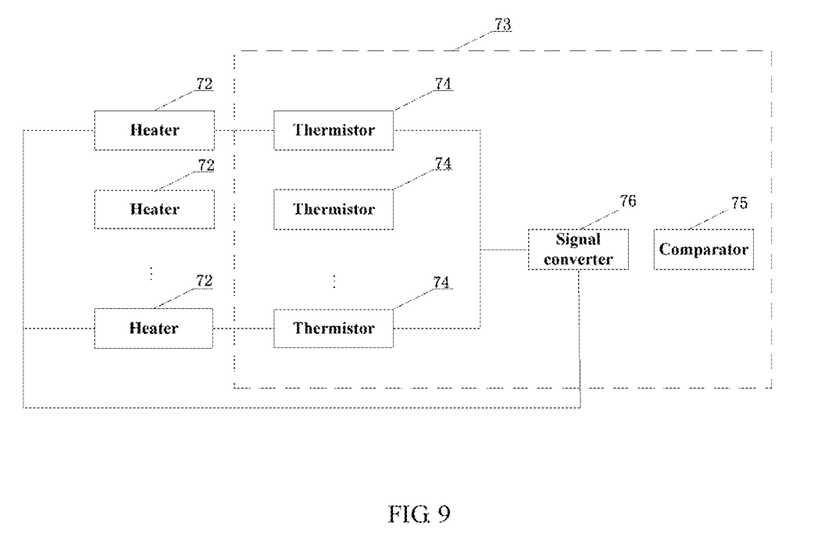
FIG. 9 is a structural schematic diagram of another heating apparatus provided by an embodiment of the present invention.

Referring to FIG. 9, the temperature controller 73 may further comprise a signal converter 76. The signal converter 76 is connected to at least one thermistor 74 and the comparator 76 till the comparator 75 is connected to the temperature sensor 74, and is used for converting a current resistance value output by each thermistor into a current temperature value of the corresponding heater 72 and outputting the current temperature of each heater 72 to the comparator 75.

In the same way, the comparator 75 may delay the start of a period of time after controlling the target heater to continue to heat or stop heating, for example, the delay time may be 1 minute. After the delay time has elapsed, the current temperature of the target heater, which is converted by the signal converter 76, continues to be collected. In an embodiment of the present invention, referring to FIG. 10, the heating apparatus may further include an input unit 77 which is connected to the comparator 75 and used for inputting a set temperature and/or a delay time to the comparator 75.

Figure 10:
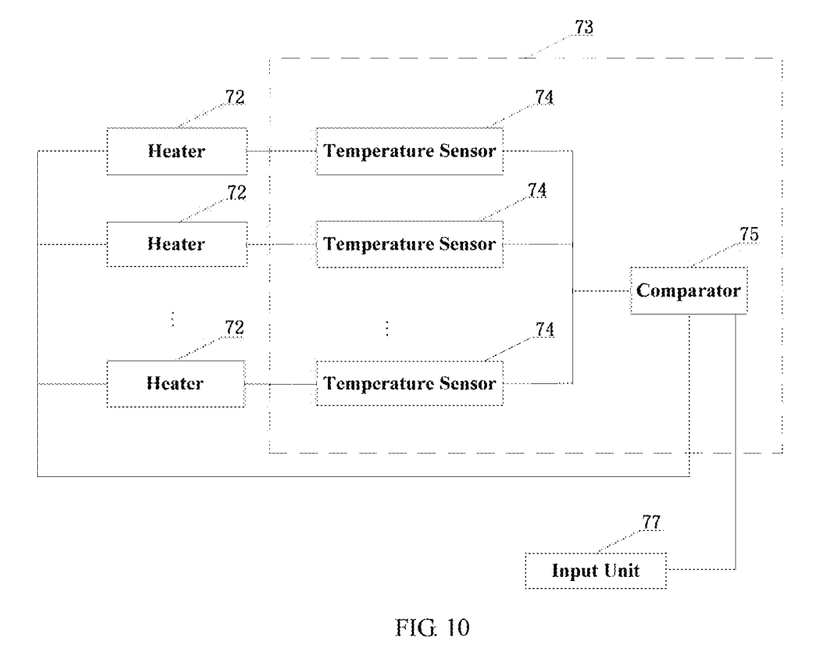
FIG. 10 is a structural schematic diagram of a further heating apparatus provided by an embodiment of the present invention.

The set temperature may be determined based on the nature of the liquid contained in the container 71 and the purpose of detection. Taking the liquid contained in the container 71 being blood as an example, the blood is used for analysis and monitoring of a thromboelastogram, and therefore, the set temperature may be 37° C.

The more the number of heaters 72 provided on the container 71, the faster the heating speed of the liquid contained in the container 71, and the better the heating effect. When the number of the heaters 72 is too large, the cost of the heating apparatus may be increased accordingly. Therefore, preferably, three heaters are provided.

In one embodiment of the invention, the at least one heater 72 may be arranged at the bottom of the container 71 or at the side of the container 71.

Preferably, in order to ensure uniform heating of the liquid contained in the container 71, the at least one heater 72 is uniformly arranged at the bottom of the container 71.

In an embodiment of the invention, to further achieve uniform heating of the liquid in the container 71, the at least one heater includes: a ceramic heater.

Figure 11:
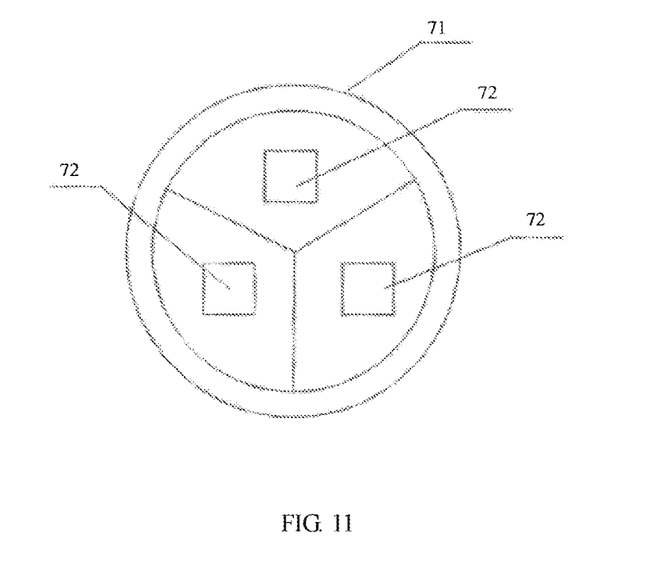
FIG. 11 is a schematic diagram in which three temperature sensors are arranged at the bottom of the container uniformly as provided by an embodiment of the present invention.

The distribution of the heater will be described by taking the number of heaters being three as an example. Referring to FIG. 11, the three heaters are uniformly distributed at the bottom of the container 71.

In an embodiment of the present invention, the shape of the container 71 may be any one of a circle, a polygon, and an irregular figure.

An embodiment of the present invention further provides a blood coagulation analysis system, comprising the heating apparatus according to any one of the above embodiments and a thrombelastography device, wherein the thrombelastography device is used for performing coagulation analysis on blood in the container of the heating apparatus.

In an embodiment of the present invention, the blood coagulation analysis system may further comprise a drive device and a pallet, wherein the drive device is used for driving the pallet to rotate; and the container of the heating apparatus is fixed on the pallet.

In one embodiment, the thrombelastography device included in the blood coagulation analysis system is any one of the various embodiments of the thrombelastography device described above or any combination thereof.

Figure 12:
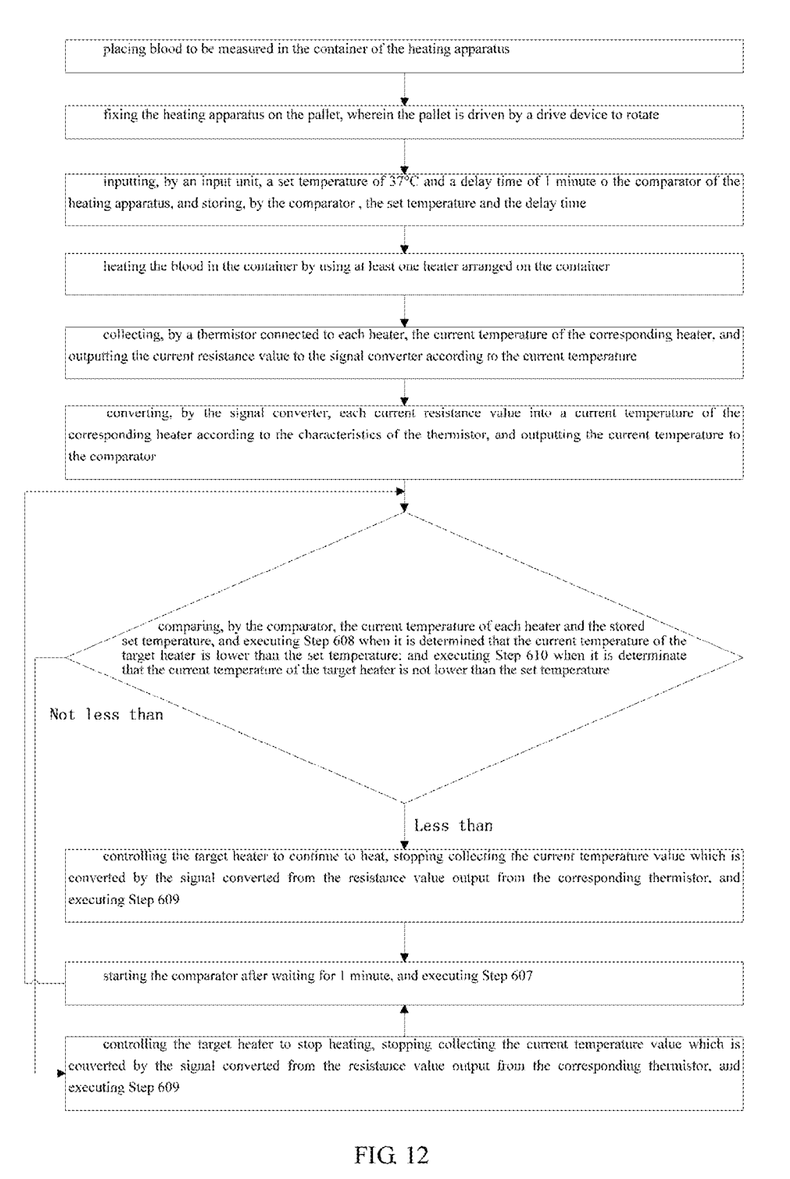
FIG. 12 is a working flowchart of coagulation analysis provided by an embodiment of the present invention.

In order to make the heating apparatus and the blood coagulation analysis system provided by the present invention clearer, the workflow will be described in detail by taking the in which blood is heated by the heating apparatus and the blood heated in the heating apparatus is subjected to blood coagulation analysis by using the thrombelastography device as an example. Referring to FIG. 12, the workflow comprises the following steps 601-610.

Step 601: placing blood to be measured in the container of the heating apparatus;

Step 602: fixing the heating apparatus on the pallet, wherein the pallet is driven by a drive device to rotate.

Steps 601 to 602 are preparations for heating the blood to perform coagulation analysis.

Step 6033: inputting, by an input unit, a set temperature of 37° C. and a delay time of 1 minute o the comparator of the heating apparatus, and storing, by the comparator, the set temperature and the delay time.

Step 604: heating the blood in the container by using at least one heater arranged on the container.

Step 605: collecting, by a thermistor connected to each heater, the current temperature of the corresponding heater, and outputting the current resistance value to the signal converter according to the current temperature.

Step 606: converting, by the signal converter, each current resistance value into a current temperature of the corresponding heater according to the characteristics of the thermistor, and outputting the current temperature to the comparator.

Different types of thermistors have different characteristics. Therefore, it is necessary to know the characteristics of the thermistor in advance, that is, the correspondence between the resistance value and the temperature value, so that the signal converter can convert the resistance value into the temperature of the corresponding heater more accurately, thereby ensuring that the comparator can determine the control over the heater more accuracy and further improving the accuracy in blood coagulation analysis.

Step 607: comparing, by the comparator, the current temperature of each heater and the stored set temperature, and executing Step 608 when it is determined that the current temperature of the target heater is lower than the set temperature; and executing Step 610 when it is determinate that the current temperature of the target heater is not lower than the set temperature.

Step 608: controlling the target heater to continue to heat, stopping collecting the current temperature value which is converted by the signal converted from the resistance value output from the corresponding thermistor, and executing Step 609.

Step 609: starting the comparator after waiting for 1 minute, and executing Step 607.

Step 610: controlling the target heater to stop heating, stopping collecting the current temperature value which is converted by the signal converted from the resistance value output from the corresponding thermistor, and executing Step 609.

The above steps 603 to 610 are the process for heating the blood in the container by the heating apparatus. During this process, after the temperature of the heater is kept at the set temperature for a period of time, the temperature of the blood at this time can be determined to reach the set temperature. In this case, At this time, the thrombelastography device can perform blood coagulation analysis on the blood to produce a thromboelastogram. This time period may be set based on the empirical value, for example, two minutes.

The thromboelastogram is an index that reflects the dynamic changes of blood coagulation (including formation rate of fibrin, dissolved state and the firmness of condensed state, and elasticity).

Various embodiments of the heating apparatus of the present invention may at least achieve the following beneficial effects:

1. in the embodiment of the present invention, the liquid in the container is heated by contacting at least one heater to the container. The current temperature of each heater is collected by the temperature controller. The heater is subjected to heating control according to the pre-stored set temperature to ensure that the temperature of the heater is kept to a preset temperature. The heater can ensure, by heat transfer, that the liquid in the container is also kept to the set temperature, thereby achieving automatic heating control and further reducing the cost.

2. In the embodiment of the present invention, the thermistor which serves as a temperature sensor acquires the temperature of the heater. Due to the temperature sensitive nature of the thermistor, the efficiency of collecting the current temperature of the heater can be improved.

3. In the embodiment of the present invention, the heating apparatus comprises the input unit which is connected to the comparator and used for inputting the set temperature to the comparator, and therefore, different set temperatures can be input according to different liquids and different purposes, and the flexibility of the heating apparatus is improved.

4. In the embodiment of the present invention, at least one heater is arranged at the bottom of the container uniformly, and therefore the liquid in the container can be heated uniformly, and the liquid measurement accuracy may be improved.

5. In the embodiment of the present invention, the liquid in the container can be heated by the ceramic heater. According to the high-efficiency heating uniformity of the ceramic heater, the liquid in the container can be further heated uniformly and the heating efficiency can be improved.

It will be understood that the "processor" or "processing module/unit" described herein may be any software, hardware, firmware or a combination thereof, which can execute appropriate program instructions, arithmetic operations, data processing and/or control operations, and the like, such as a computer, a central processing unit, or the like. They may be a centralized processing system or a distributed processing system.

It can be appreciated that, while the relationship terms "first", "second" and so on may be used herein to distinguish one entity or operation from another, it does not require or imply such a relation or sequence between these entities or operations. Further, the terms "include", "comprise" or any variation thereof are intended to cover an nonexclusive containing, such that a process, a method, an item or a device containing a series of elements not only includes these elements, but also includes other elements that are not set forth specifically, or also includes an inherent element of such a process, method, item or device. Without further limitation, an element defined by a phrase "include a" does not mean that other elements are excluded from the process, method, item or device.

It will be understood by those skilled in the art that: all or part of the steps of implementing the foregoing method embodiments may be performed by hardware related to program instructions. The aforementioned program can be stored in a computer readable storage medium. The program, when executed, performs the steps including the above method embodiments; the foregoing storage medium includes various kinds of media, such as a ROM, a RAM, a magnetic disk, or an optical disk, that can store program codes.

Aspect of Invention

The various aspects numbered below further provide the disclosure of the present invention.

1. A thrombelastography device which consists of a plurality of thrombelastography device splits that are horizontally arranged in parallel, wherein each of the thrombelastography device splits comprises:
   a worktable which is used for supporting a container for containing blood and comprises a power device for driving the container to rotate;
   a rack fixed on the worktable;
   a test bar which is located above the container, able to be at least partially inserted into the blood in the container and rotatably connected to the rack, wherein the side surface of the test bar is further provided with a reflective surface; and
   a tester which is fixedly connected to the rack and provided with a first through hole that allows the test bar to passes through and is arranged vertically, and at least two second through holes which are communicated with the first through hole and are arranged horizontally, wherein the reflective surface is located in the first through hole, a light emitting device and a light receiving device are arranged inside the at least two second through holes respectively, the light emitting device is able to emit light to the reflective surface, and the light receiving device is able to receive light reflected by the reflective surface.

2. The thrombelastography device according to aspect 1, wherein the rack comprises a first support fixedly connected to the tester and a second support fixedly connected to the test bar, wherein the first support comprises two upright columns which are fixed on the tester and arranged vertically, and a first crossbeam which is used for connecting the two upright columns and arranged horizontally; the second support comprises an opening through which the first crossbeam passes, and a second crossbeam which is located right above the first crossbeam and is arranged horizontally; a top cone which protrudes downward is arranged in the middle of the lower surface of the second crossbeam; a jewel bearing is arranged on the upper surface of the first crossbeam; the jewel bearing is located below the top cone; the top cone is in point contact with a concave hole in the jewel bearing.

3. The thrombelastography device according to aspect 2, wherein magnets are oppositely arranged on the upper surface of the first crossbeam and the lower surface of the second crossbeam, and the opposite surfaces of the magnets have like magnetic poles.

4. The thrombelastography device according to aspect 3, wherein two reflective surfaces are arranged to be parallel to each other; four second through holes are arranged to respectively accommodate two light emitting devices or two light receiving devices respectively.

5. The thrombelastography device according to aspect 4, wherein a hollow light guide column is arranged in the second through holes respectively; the light emitting device or the light receiving device is located in the light guide column; the light emitting device is a light emitting diode.

6. The thrombelastography device according to aspect 5, wherein a photoelectric source is connected to the light receiving device; an amplified circuit board and an AD converter are electrically connected to the photoelectric source in sequence; the AD converter is connected to the processor.

7. The thrombelastography device according to aspect to 6, wherein a light blocking sheet which is able to block the light guide column from the reflective surface is arranged at one end, close to the first through hole, of the light guide column; the light blocking sheet is provided with a light outgoing hole; the light blocking sheet is able to limit the light to pass through the light outgoing hole only.

8. The thrombelastography device according to aspect 7, further comprising a hair spring whose inner ring is statically connected to an outer circumferential surface of the test bar and whose outer ring is statically connected to the upright column.

9. The thrombelastography device according to aspect 2, further comprising a position correction device which is connected to the test bar and used for generating, when the test bar rotates away from a balanced position, an acting force for rotating the test bar back to the balanced position.

10. The thrombelastography device according to aspect 9, wherein the position correction device comprises at least one hair spring, wherein an inner ring of each of the hair springs is fixedly connected to an outer circumferential surface of the test bar, and an outer ring of each of the hair springs is fixedly connected to the upright column.

11. The thrombelastography device according to claim 10, wherein when the position correction device comprises at least two hair springs, the spiral direction of at least one hair spring among at least two hair springs from the inner ring to the outer ring is opposite to the spiral direction of the other hair spring from the inner ring to the outer ring.

12. The thrombelastography device according to aspect 10, wherein the position correction device further comprises at least one zero setting module, wherein
  each zero setting module corresponds to one hair spring; and
  one end of each zero setting module is fixedly connected to the upright column, and the other end thereof is fixedly connected to different positions on the outer ring of the corresponding hair spring in an adjustable manner, so as to adjust the balanced position.

13. A position correction device for a thrombelastography device, wherein the thrombelastography device comprises a rack and a test bar; the rack is connected to one end of the test bar; the rack is used for supporting the test bar, such that the other end of the test bar can be placed in measured blood;
  the test bar is configured to be able to rotate under a driving force of the measured blood; and
  the position correction device is connected to the test bar and used for generating, when the test bar rotates away from a balanced position, an acting force for rotating the test bar back to the balanced position.

14. The position correction device according to aspect 13, further comprising at least one hair spring, wherein an inner ring of each of the hair springs is fixedly connected to the outer circumferential surface of the test bar, and an outer ring of each of the hair springs is fixedly connected to the rack.

15. The position correction device according to aspect 14, wherein, when the position correction device comprises at least two hair springs, the spiral direction of at least one hair spring among the at least two hair springs from the inner ring to the outer ring is opposite to the spiral direction of the other hair spring from the inner ring to the outer ring.

16. The position correction device according to claim 14, wherein the position correction device further comprises at least one zero setting module, wherein
  each zero setting module corresponds to one hair spring; and
  one end of each zero setting module is fixedly connected to the rack, and the other end thereof is fixedly connected to different positions on the outer ring of the corresponding hair spring in an adjustable manner, so as to adjust the balanced position.

17. The thrombelastography device, comprising a rack, a test bar and the correction device according to any one of aspects 13 to 16.

18. A use method for the thrombelastography device according to aspect 17, comprising:
  supporting the test bar by the rack, such that one end of the test bar is placed in the measured blood;
  driving the test bar by the measured blood, such that the test bar rotates; and
  generating, by the position correction device when the test bar rotates away from a balanced position, an acting force for restoring the test bar to the balanced position.

19. A heating apparatus, comprising:
  a container for containing liquid;
  at least one heater which is in contact with the container and used for heating the liquid in the container; and
  a temperature controller which is connected to the at least one heater, and used for collecting a current temperature of each heater and performing heating control on each heater according to the current temperature of each heater and a pre-stored set temperature.

20. The heating apparatus according to aspect 19, wherein the temperature controller comprises:
  at least one temperature sensor which is connected to the at least one heater in a one-to-one correspondence manner, and used for collecting a current temperature of the heater connected thereto, and outputting the collected current temperature of each heater to a comparator; and
  the comparator which is connected to the at least one temperature sensor and at least one heater, and used for performing heating control on each heater according to the current temperature of each heater and the pre-stored set temperature.

21. The heating apparatus according to aspect 20, wherein the temperature sensor comprises a thermistor which is used for outputting a current resistance value to a signal converter according to the current temperature of the heater connected to the temperature sensor; and
  the temperature controller further comprises the signal converter which is connected to the thermistor and the comparator and is used for outputting the current temperature of each heater to the comparator according to the current resistance value outputted by each thermistor.

22. The heating apparatus according to aspect 20 or 21, further comprising an input unit which is connected to the comparator and used for inputting the set temperature to the comparator.

23. The heating apparatus according to any one of claims 19 to 21, wherein the at least one heater is arranged at the bottom of the container.

24. The heating apparatus according to aspect 23, wherein at least one heater is arranged at the bottom of the container uniformly.

25. The heating apparatus according to any one of claims 19 to 21, wherein the at least one heater includes a ceramic heater.

26. The heating apparatus according to any one of aspects 19 to 21, comprising the three heaters.

27. A blood coagulation analysis system, comprising the heating apparatus according to any one of claims 19 to 26 and a thrombelastography device, wherein
the thrombelastography device is used for performing coagulation analysis on blood in the container of the heating apparatus.

28. The coagulation analysis system according to aspect 27, further comprising a drive device and a pallet, wherein
the drive device is used for driving the pallet to rotate; and the container of the heating apparatus is fixed on the pallet.

29. The coagulation analysis system according to aspect 27, wherein the thrombelastography device is the thrombelastography device according to any one of aspects 1 to 12 and 17.

30. A thrombelastography device, consisting of a plurality of thrombelastography device splits that are horizontally arranged in parallel, wherein each of the thrombelastography device splits comprises:
a worktable which is used for supporting a container which is arranged on the upper surface of the worktable and used for containing blood and comprises a power device or driving the container to rotate, wherein a heating apparatus and a controller that can control the heating apparatus to heat the blood in the container to a set temperature are arranged in the container;
a rack fixed on the worktable;
a test bar which is located right above the container, able to be at least partially inserted into the blood in the container and rotatably connected to the rack, wherein the side surface of the test bar is further provided with a vertical reflective surface; and
a tester which is fixedly connected to the support and provided with a first through hole that allows the test bar to passes through and is arranged vertically, and at least two second through holes which are communicated with the first through hole and are arranged horizontally, wherein the reflective surface is located in the first through hole, a light emitting device and a light receiving device are arranged inside the at least two second through holes respectively, the light emitting device is able to emit straight light to the reflective surface, and the light receiving device is able to receive light reflected by the reflective surface; and
a processor which is able to convert the amount of straight light received by the light receiving device into parameter information reflecting blood coagulation, the parameter information being directly proportional to the amount of light received by the light receiving device.

31. The thrombelastography device according to aspect 30, wherein the rack comprises a first support fixedly connected to the tester and a second support fixedly connected to the test bar, wherein the first support comprises two upright columns which are fixed on the tester and arranged vertically, and a first crossbeam which is used for connecting the two upright columns and arranged horizontally; the second support comprises an opening through which the first crossbeam passes, and a second crossbeam which is located right above the first crossbeam and is arranged horizontally; a top cone which protrudes downward is arranged in the middle of the lower surface of the second crossbeam; a jewel bearing is arranged on the upper surface of the first crossbeam; the jewel bearing is located below the top cone; the top cone is in point contact with a concave hole in the jewel bearing.

It should be noted that each of the above aspects 2 to 12 may be combined with aspects 30 and 31, respectively.

It should be noted that the above contents are only preferred embodiments of the present invention, and used only for describing the technical solutions of the present invention, rather than limiting the protection scope of the present invention. Any modifications, equivalents, improvements, etc. made within the spirit and principle of the present invention should be included within the protection scope of the present invention.

The invention claimed is:
1. A position correction device for a thrombelastography device, wherein the position correction device comprises:
a test bar;
a rack, the rack is connected to a first end of the test bar and supports the test bar, a second end of the test bar is placed in measured blood; the test bar is configured to rotate under a driving force of the measured blood; and
at least two hair springs, an inner ring of each of the at least two hair springs is fixedly connected to an outer circumferential surface of the test bar, and an outer ring of each of the at least two hair springs is fixedly connected to the rack, the spiral direction of a first hair spring of the at least two hair springs from the inner ring to the outer ring is opposite to the spiral direction of a second hair spring of the at least two hair springs from the inner ring to the outer ring, wherein
the position correction device is configured to generate, when the test bar rotates away from a balanced position, an acting force for rotating the test bar back to the balanced position.

2. The position correction device according to claim 1, wherein the position correction device further comprises at least two zero setting modules, wherein
each of the at least two zero setting modules corresponds to each of the at least two hair springs; and
a first end of each of the at least two zero setting modules is fixedly connected to the rack; and
a second end of each of the at least one two setting modules is fixedly connected to different positions on the outer ring of the corresponding hair spring in an adjustable manner, so as to adjust the balanced position.

3. A thrombelastography device, comprising a rack, a test bar, and the position correction device according to claim 1.

4. A use method for the thrombelastography device according to claim 3, comprising:
supporting the test bar by the rack, such that one end of the test bar is placed in the measured blood;
driving the test bar by the measured blood, such that the test bar rotates; and
generating, by the position correction device when the test bar rotates away from a balanced position, an acting force for restoring the test bar to the balanced position.

\* \* \* \* \*